US00PP28381P3

(12) United States Plant Patent
Suphachadiwong

(10) Patent No.: US PP28,381 P3
(45) Date of Patent: Sep. 12, 2017

(54) ***DENDROBIUM* PLANT NAMED 'SUDEN1402'**

(50) Latin Name: ***Dendrobium* hybrid Sw.**
Varietal Denomination: Suden1402

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 54 days.

(21) Appl. No.: 14/757,342

(22) Filed: Dec. 18, 2015

(65) Prior Publication Data

US 2016/0192568 P1 Jun. 30, 2016

(30) Foreign Application Priority Data

Dec. 29, 2014 (QZ) ..... PBR 2014/3611

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Samuel R. McCoy, Jr.

(57) ABSTRACT

A new and distinct *Dendrobium* cultivar named 'Suden1402' which is characterized by the combination of large and long-lasting flowers, with a nearly pure white general tonality, as well as the stability of these characteristics from generation to generation.

3 Drawing Sheets

Latin name of the genus and species: The Latin name of the genus and species of the novel variety disclosed herein is *Dendrobium* hybrid Sw.

Variety denomination: The inventive variety of *Dendrobium* disclosed herein has been given the variety denomination 'Suden1402'.

CROSS REFERENCE TO RELATED APPLICATIONS

This application claims priority to the Community Plant Variety Rights application number 2014/3611, filed Dec. 29, 2014, which is herein incorporated by reference.

BACKGROUND OF THE INVENTION

Parentage: The *Dendrobium* variety 'Suden1402' originated as a naturally occurring mutation of the cultivar *Dendrobium* 'Sonia' (not patented). The inventor routinely discovers mutations of 'Sonia' at his greenhouse operation in Banghra, Thailand, and has discovered a number of mutations which exhibit near-white flowers. The variety now called 'Suden1402' was discovered in March of 2008 as a whole-plant mutation derived from a stem cutting of 'Sonia'. Several of said near-white mutations were asexually reproduced and grown to a mature size for further observation and 'Suden1402' was selected for its large, white flowers and long-lasting inflorescence.

Asexual Reproduction: Asexual reproduction of the new cultivar 'Suden1402', by way of mericloning, was first initiated in February of 2009 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through five subsequent generations, the unique features of this cultivar have proven to be stable and true to type.

SUMMARY OF THE INVENTION

The cultivar 'Suden1402' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Suden1402'. These characteristics in combination distinguish 'Suden1402' as a new and distinct *Dendrobium* cultivar:

1. *Dendrobium* 'Suden1402' exhibits a white general tonality of the flower; and
2. *Dendrobium* '*Suden*1402' exhibits large flowers; and
3. *Dendrobium* 'Suden 1402' exhibits long lasting flowers.

BOTANICAL DESCRIPTION OF THE PLANT

Figure 1:
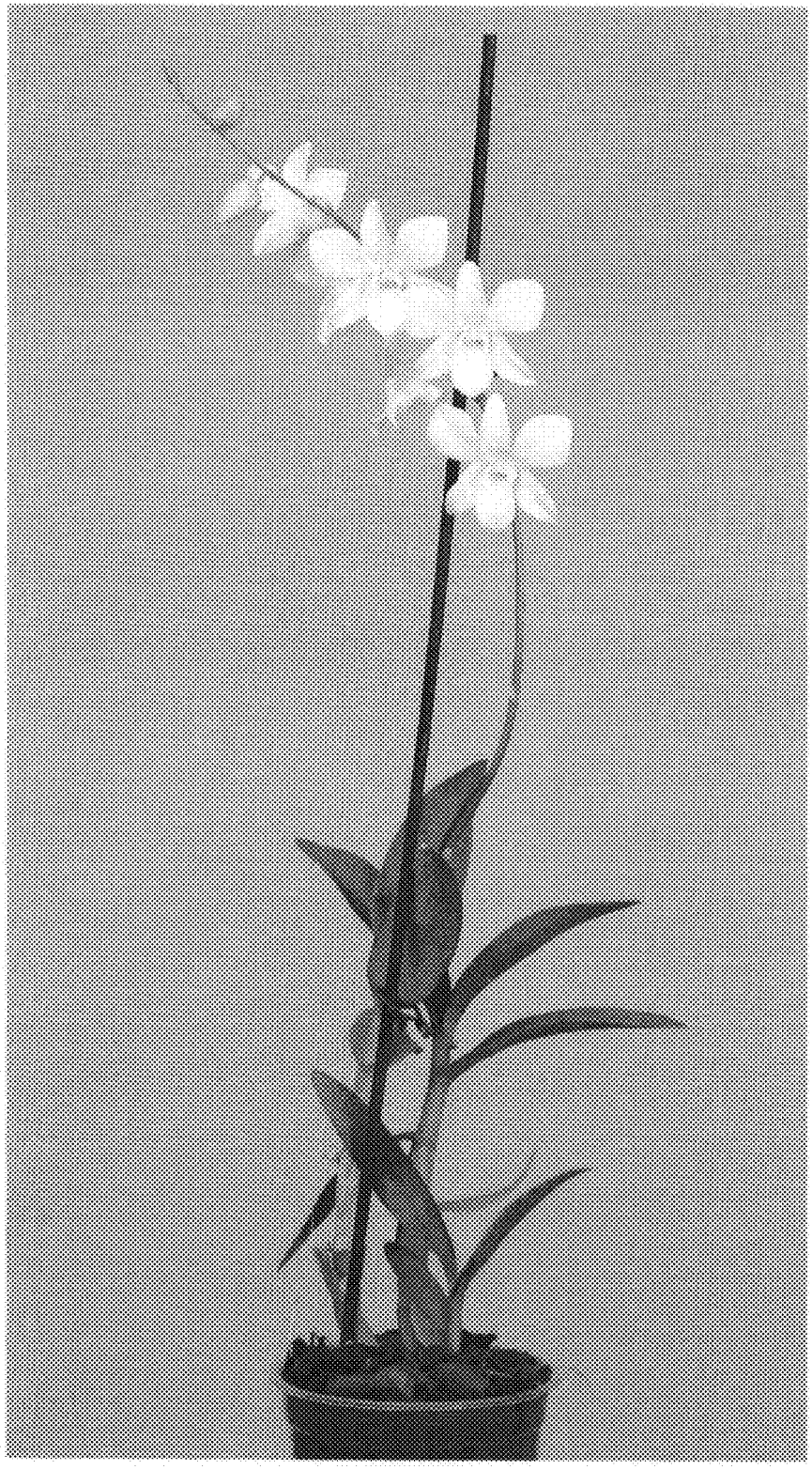
FIG. 1 illustrates, as nearly true as it is reasonably possible to make the same in color photographs of this type, an exemplary plant of 'Suden1402' grown in a commercial greenhouse in Honselersdijk, the Netherlands. This plant, grown in a 12 cm nursery container, is approximately 6 months old from a rooted young plant.
Figure 2:
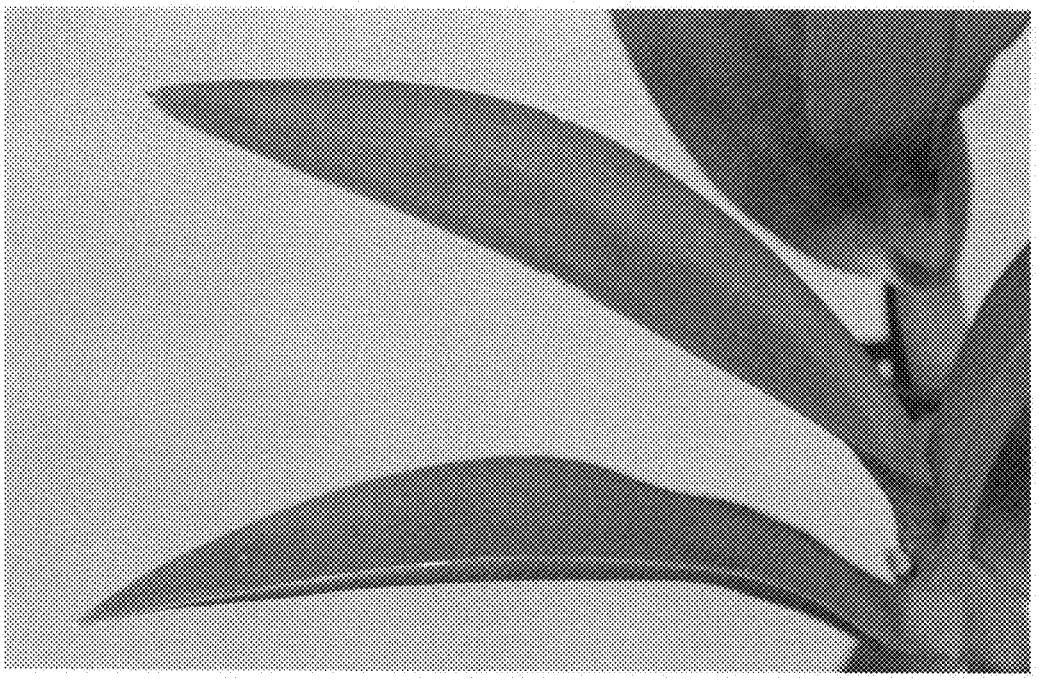
FIG. 2 illustrates, as nearly true as it is reasonably possible to make the same in color photographs of this type, the typical foliage of 'Suden1402'.
Figure 3:
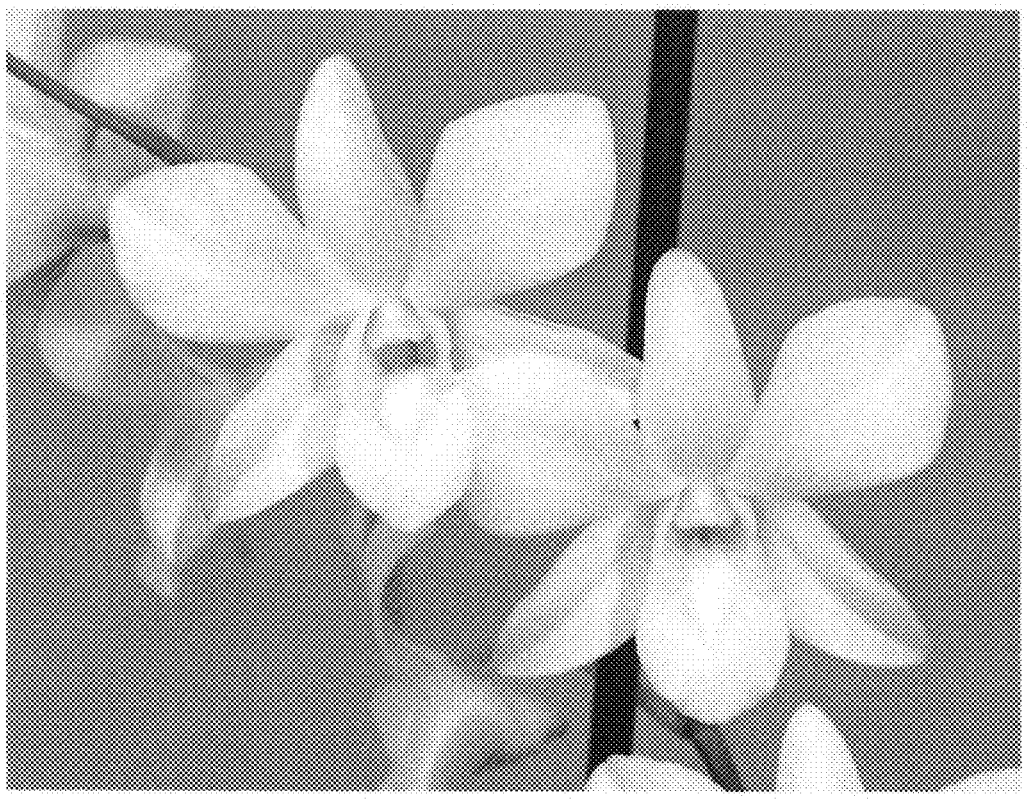
FIG. 3 illustrates, as nearly true as it is reasonably possible to make the same in color photographs of this type, the typical flowers of 'Suden1402'.

The following observations and measurements made in October of 2015 describe averages from a sample set of six specimens of 6 month-old 'Suden1402' plants grown in 12 cm nursery pots in a greenhouse in Honselersdijk, the Netherlands. Temperatures ranged from approximately 26 to 30 degrees Celsius. The light sum was set at 5 moles per day and the plant was given shading and artificial light in order to achieve the light sum of 5 moles per day.

Those skilled in the art will appreciate that certain characteristics will vary with older or, conversely, with younger plants. 'Suden1402' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'Suden1402' and comparisons with other varieties of *Dendrobium* are provided below.

Plant description:

*Growth habit*.—Perennial; sympodial, upright. Multiple leafy pseudobulbs growing from base, with flowers in terminal inflorescences, carried above the leaf plane.

*Average height from base (plant grown in hanging basket, so no soil line present) to top of foliage*.—32.8 cm.

*Average height from base (plant grown in hanging basket, so no soil line present) to top of flowers*.—66.1 cm.

*Plant spread*.—Average of 24.2 cm.

*Growth rate*.—Moderate.

*Plant vigor*.—Moderate.

*Propagation details*.—Tissue culture propagation is performed using meristem culture. Meristematic tissue is harvested from the center of a newly-emerged vegetative bud and grown on by constant agitation in a nutrient rich liquid until the cell mass is large enough to be split into small sections. These sections are either rooted and grown into young plants for finishing in nursery pots or the tissue culture process is repeated to produce more clones.

*Time to initiate roots*.—Mericloning requires 18 months to yield a propagule which is ready to be rooted, or "deflasked", in soilless propagation media. After deflasking the micropropagule, an additional 9 to 12 months is required to produce a fully rooted plant under average temperatures ranging between 26 and 30 degrees Celsius.

*Disease and pest resistance or susceptibility*.—Similar to other *Dendrobium* varieties.

*Environmental tolerances*.—Adapt to at least USDA Zones 11 and 12 and temperatures as high as 40 degrees Celsius; high tolerance to rain; moderate tolerance to wind.

Root system:

*General*.—Moderately dense rooting.

*Dimensions, mature roots*.—11.1 cm long with a diameter of 0.15 cm, on average.

*Texture*.—Fleshy; non-fibrous.

*Color*.—Green-white, near RHS 157A; older roots are yellow-white, near RHS 158A and 158B.

Stem:

*Branching habit*.—Sympodial; pseudobulbs growing from base; no lateral branches present.

*Number of primary (main) stems per plant*.—Three.

*Number of secondary (lateral) branches per plant*.—None.

*Longitudinal section shape*.—Narrow elliptic to oblanceolate; axially ribbed.

*Cross section shape*.—Elliptical.

*Length*.—23.5 cm.

*Diameter*.—Averaging 1.8 cm at the widest point and 1.6 cm at the narrowest point.

*Internode length*.—4.1 cm.

*Luster*.—Matte.

*Aspect*.—Average angle is approximately 75 degrees from horizontal plane.

*Strength*.—Strong.

*Color, juvenile*.—Yellow-green, near RHS 152B.

*Color, mature*.—Yellow-green, near RHS 152B.

*Color at internodes*.—Yellow-green, near RHS 152B.

*Pubescence*.—Glabrous.

Foliage:

*Arrangement*.—Distichous.

*Quantity*.—Approximately 13 leaves per plant.

*Lamina*.—Dimensions — 13.6 cm long and 4.3 cm wide, on average. Shape — Ovate to narrow ovate. Aspect — Very slightly concave. Apex — Acute. Base — Sheathing. Margin — Entire. Pubescence, texture and luster of adaxial surface — Glabrous, smooth, and moderately glossy. Pubescence, texture and luster of abaxial surface — Glabrous, smooth, and matte. Color — Juvenile foliage, adaxial surface — Green, nearest to in between RHS 137B to 143A. Juvenile foliage, abaxial surface — Yellow-green, near RHS 144A and 146A. Mature foliage, adaxial surface — Green to yellow-green, in between near-RHS 137A and 146A. Mature foliage, abaxial surface — Green, near RHS 138B. Venation — Parallel. Venation color, adaxial surface — Green to yellow-green, in between near RHS 137A and 146A. Venation color, abaxial surface — Green, near RHS 137D.

*Sheath*.—Dimensions — 3.3 cm long and 1.6 cm wide, on average. Color — Yellow-Green, near RHS 147C to 147D.

*Petiole*.—No petioles present, leaves sessile.

Inflorescence:

*Inflorescence arrangement*.—Simple terminal raceme with flowers borne along the peduncle.

*Natural flowering season*.—Autumn into winter.

*Time to flower*.—Approximately 10 months.

*Inflorescence quantity*.—One.

*Flowers per inflorescence*.—Average of 9; 8 open flowers and 1 bud.

*Inflorescence height*.—Approximately 30.2 cm (measured from base of lowest flower to top of upper flower).

*Inflorescence diameter*.—Approximately 11.0 cm.

*Peduncle*.—Dimensions — Approximately 50.5 cm long and 0.4 cm wide. Aspect — Approximately 5 degree angle to main stem. Strength — Strong. Texture and luster — Glabrous and very slightly glossy. Color — Yellow-green, near RHS 144B and 144C.

Bud:

*Length*.—Average of 3.3 cm.

*Diameter*.—Average of 1.2 cm.

*Shape*.—Ovate; curved.

*Pubescence, texture and luster*.—Glabrous, smooth and moderately glossy.

*Color*.—Yellow-green, near RHS 145B.

Flower:

*Flower type*.—Zygomorphic (orchidaceous), typical shape for the genus *Dendrobium*.

*Flowering habit*.—Moderately floriferous.

*Shape*.—Zygomorphic, single; consisting of three sepals and three petals, one of which is transformed into a labellum.

*Aspect*.—Flowers are outward-facing.

*Height*.—Approximately 6.8 cm.

*Diameter*.—Approximately 7.3 cm.

*Depth*.—Approximately 3.4 cm.

*Fragrance*.—No fragrance.

*Lastingness*.—Up to 9 weeks from the day of opening until flower drop.

*Persistent*.—Self-cleaning.

*Petals*.—Quantity of Petals — 3; two conventional petals and one labellum. Arrangement — One lateral petal on each side, separated by the labellum. Aspect — Petals are flat; not twisting. Length — Approximately 4.7 cm. Width — Approximately 2.8 cm. Shape — Obovate to rhomboidal; slightly curled backwards. Apex — Bluntly acute. Base — Cuneate. Margin — Entire; no undulation. Pubescence, texture and luster of upper surface — Glabrous, velvety and matte. Pubescence, texture and luster of lower surface — Glabrous, velvety and matte. Color when opening, upper surface — White, lighter than near RHS NN155D; base and apex are white, near RHS NN155D. Color when opening, lower surface — White, lighter than near RHS NN155D; base and apex are white, near RHS NN155C. Color when fully opened, upper surface — White, lighter than near RHS NN155D. Color when fully opened, lower surface — White, lighter than near RHS NN155D. Fading, upper surface — Not fading. Fading, lower surface — Not fading. Venation color, fully opened, upper surface — White, lighter than near RHS NN155D. Venation color, fully opened, lower surface — White, lighter than near RHS NN155D.

*Labellum*.—Shape — Central lobe — Obovate. Lateral lobes — Ovate. Length — Central lobe — Approximately 3.6 cm. Lateral lobes — Approximately 1.5 cm. Width — Central lobe — Approximately 2.1 cm. Lateral lobes — Approximately 1.6 cm. Apex — Central lobe — Very broad acute. Lateral lobes — Obtuse. Base — Central lobe — Cuneate. Lateral lobes — Cuneate. Aspect — Central lobe — Not twisting. Lateral lobes — Not twisting. Margin — Central lobe — Entire; moderately undulate. Lateral lobes — Finely irregular denticulate; not undulate. Texture and luster of upper surface — Central lobe — Glabrous, velvety, and matte. Lateral lobes — Glabrous, velvety, and matte. Texture and luster of lower surface — Central lobe — Glabrous, slightly velvety, and slightly glossy. Lateral lobes — Glabrous, slightly velvety, and slightly glossy. Color when opening, upper surface — Central lobe — White, near RHS NN155A, with a narrow purple-tinged margin of the callosities, near RHS 75D. Lateral lobes — Green-white, near RHS 157D, with a yellow-green base, near RHS 145D. Color when opening, lower surface — Central lobe — White, near RHS 155C, with a lighter central band, near RHS NN155D. Lateral lobes — Yellow-green, slightly lighter than near RHS 145D. Color when fully opened, upper surface — Central lobe — White, lighter than near RHS NN155D, with a narrow purple-tinged margin of the callosities, near RHS 75D, and a small green-yellow blotch on each side of the callosities, near RHS 1D. Lateral lobes — White, near RHS NN155C and NN155D. Color when fully opened, lower surface — Central lobe — White, near RHS NN155D. Lateral lobes — White, near RHS NN155C and NN155D. Fading, upper surface — Not fading. Fading, lower surface — Not fading. Venation color, fully opened, upper surface — Central lobe — White, lighter than near RHS NN155D, with a narrow purple-tinged margin of the callosities, near RHS 75D, and a small green-yellow blotch on each side of the callosities, near RHS 1D. Lateral lobes — White, near RHS NN155C and NN155D. Venation color, fully opened, lower surface — Central lobe — White, near RHS NN155D. Lateral lobes — White, near RHS NN155C and NN155D. Labellum eye — Not present. Callosities — Location — Centrally placed on the central lobe of the labellum. Length — 2.4 cm, on average. Width — 0.6 cm, on average. Color — White, near RHS NN155D.

*Spurs*.—Quantity — Average of 1. Length — Approximately 0.7 cm. Diameter — Approximately 0.3 cm. Vertical height — Approximately 0.7 cm. Shape — Short triangular. Apex — Bluntly acute. Base — Broad Cuneate. Pubescence, texture and luster — Glabrous, smooth, and moderately glossy. Color — Yellow-green, near RHS 145C.

*Sepals*.—Quantity — Average of 3 unfused sepals. Arrangement — One dorsal sepal and two lateral sepals. Length — Dorsal sepal — Approximately 4.2 cm. Lateral sepals — Approximately 4.2 cm. Width — Dorsal sepal — Approximately 1.7 cm. Lateral sepals — Approximately 2.1 cm. Shape — Dorsal sepal — Elliptical; slightly curled backwards; not twisting. Lateral sepals — Elliptical; slightly curled downward and slightly curled backwards; not twisting. Apex — Dorsal sepal — Acute. Lateral sepals — Acute. Base — Dorsal sepal — Broad cuneate. Lateral sepals — Broad cuneate. Margin — Dorsal sepal — Entire; not undulate. Lateral sepals — Entire; not undulate. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and very slightly glossy. Lateral sepals — Glabrous, velvety, and very slightly glossy. Color when opening, upper surface — All sepals are white, near RHS NN155B. Color when opening, lower surface — All sepals are white, near RHS NN155A. Color when fully opened, upper surface — All sepals are white, lighter than near RHS NN155D. Color when fully opened, lower surface — All sepals are white, near RHS NN155D. Fading, upper surface —

Not fading. Fading, lower surface — Not fading. Venation color, fully opened, upper surface — All sepals are white, near RHS NN155D. Venation color, fully opened, lower surface — All sepals are white, near RHS NN155D.

*Pedicels*.—Length — Approximately 4.4 cm. Diameter — Approximately 0.3 cm. Angle — Approximately 45 degree angle to peduncle axis. Strength — Moderately strong. Texture and luster — Glabrous and moderately glossy. Color — Green-white, near RHS 157D; proximal end is yellow-green to green-white, between near RHS 148D and 157A.

Reproductive organs:

*Column*.—Length — Approximately 0.7 cm. Diameter — Approximately 1.0 cm. Color — White, near RHS NN155C.

*Anther cap*.—Length — Approximately 0.3 cm. Width — Approximately 0.25 cm. Color — Yellow-green, nearest to RHS 150D.

*Ovary*.—Position — Inferior. Diameter — Approximately 0.4 cm. Color — Green-white, near RHS 157D.

*Pollinia color*.—Yellow, near RHS 11A.

Seed and fruit: No fruit and seed production has been detected to date.

COMPARISONS WITH THE PARENT PLANT

Plants of the new cultivar 'Suden1402' are similar to the parent, *Dendrobium* 'Sonia', in most horticultural characteristics. However 'Suden1402' differs from the parent in the following characteristics:

1. The flowers of 'Suden1402' are white and sometimes exhibit a slight pink hue, whereas the flowers of 'Sonia' are generally dark purple and white.
2. The flowers of 'Suden1402' are larger than the flowers of 'Sonia'.
3. The flower petals of 'Suden1402' are more rounded than those of 'Sonia'.

COMPARISON WITH THE MOST SIMILAR *DENDROBIUM* CULTIVAR KNOWN TO THE INVENTOR

'Suden1402' is similar in many horticultural characteristics to the commercial variety *Dendrobium* 'SPCDW0602' (U.S. Plant Pat. No. 19,773). However 'Suden1402' differs from 'SPCDW0602' in the following characteristics:

1. The flowers of 'Suden1402' exhibit a general tonality which is very close to pure white, whereas the flowers of 'SPCDW0602' exhibit a duller white tonality.
2. The flowers of 'Suden1402' are almost pure white whereas the flowers of 'SPCDW0602' exhibit a pink hue.
3. The flowers of 'Suden1402' are larger than the flowers of 'SPCDW0602'.
4. The flower petals of 'Suden1402' are more rounded than those of 'SPCDW0602'.

That which is claimed is:

1. A new and distinct variety of *Dendrobium* plant named 'Suden1402', substantially as described and illustrated herein.

* * * * *